United States Patent [19]

Reckel et al.

[11] 4,140,662

[45] Feb. 20, 1979

[54] ATTACHMENT OF PROTEINS TO INERT PARTICLES

[75] Inventors: Rudolph P. Reckel, Bridgewater; Joanne L. Harris, Annandale, both of N.J.

[73] Assignee: Ortho Diagnostics, Inc., Raritan, N.J.

[21] Appl. No.: 781,256

[22] Filed: Mar. 25, 1977

[51] Int. Cl.$^2$ .................. A61K 39/00; C08L 89/00
[52] U.S. Cl. .......................................... 260/8; 195/63; 195/68; 260/112 R; 424/12; 424/13; 424/78; 424/177
[58] Field of Search ............... 260/8, 112 R; 424/12, 424/177

[56] References Cited

U.S. PATENT DOCUMENTS

| | | | |
|---|---|---|---|
| 3,639,558 | 2/1972 | Csizmas | 424/12 |
| 3,788,948 | 1/1974 | Kagedal et al. | 260/112 R |
| 3,857,931 | 12/1974 | Hager | 424/12 |
| 3,959,079 | 5/1976 | Mareschi et al. | 195/63 |
| 4,007,089 | 2/1977 | Smith | 260/112 R |
| 4,045,384 | 8/1977 | Dorman | 260/8 |

*Primary Examiner*—Edward M. Woodberry
*Attorney, Agent, or Firm*—Ralph T. Lilore

[57] ABSTRACT

A two-step process for achieving a covalent bond between latex polymers and immunological substances, the first of which involves reacting latex particles having a reactive carboxyl group with a diamine in the presence of an appropriate carbodiimide as the condensing agent. The resulting product, which can be designated as the modified latex, is an amide terminating in primary or secondary amino groups. This product is then reacted with the appropriate immunological reagent such as an antigen or antibody modified if necessary to contain amino groups, in the presence of a bifunctional aldehyde to result in the condensation of the amino groups of the immunological reagent to the amino groups of the modified latex via an intermediate aldehyde bridging moiety.

18 Claims, No Drawings

ATTACHMENT OF PROTEINS TO INERT PARTICLES

This invention relates to the field of diagnostic testing and more particularly to immunological and serological testing systems. Specifically, it relates to the provision of carrier particles carrying immunological reagents, i.e. antibodies or antigens covalently bonded to the particles through a bridging group for use in serological or immunological diagnostic test systems.

DESCRIPTION OF PRIOR ART

In conducting immunological tests, one skilled in the art is confronted with the prospect of attempting to discern whether or not a reaction has taken place between related immunological agents. Thus, for example, when it is sought to determine whether and how much of a particular antigen or antibody resides in a body fluid one must attempt to react the fluid suspected of containing this material with its immunological partner. If a reaction takes place, then the visualization of that reaction is evidence of the presence of the antigen or antibody in the originally tested fluid. It is, of course, known that antigens will induce the formation of antibodies in most animals. The relationship between the induced antibody and the antigen is such that when combined in the proper quantities these two materials will form a complex. One of the major problems in the diagnostic field, relative to immunological testing is that this reaction is not very often manifested in a visual event. Thus, the complex may form but might be invisible to the naked eye or may be soluble in the reaction medium.

To overcome this lack of means to characterize the reaction, the art has long employed the technique of utilizing indicator or carrier particles upon which is carried the appropriate immunological material. The types of particles used are extremely varied, ranging from biological materials such as red blood cells and tissue culture cells to immunologically inert polymeric particles.

By far the most suitable system has been the polymeric particle technique described above in which synthetic resin particles of quite small size have been used as an adsorbant onto which the appropriate antigen or antibody has been adsorbed. In this system the latex particles are usually spherical having a diameter usually in the range of 0.05 to 1.0 microns. While the latex particle system has been quite suitable and has been employed widely, nevertheless, there are certain characteristics of the system which are undesirable from the point of view of reactant specificity. For some reason, not quite understood fully, while one could have a very specific antibody adsorbed onto an immunologically inert polymeric carrier, it is possible, and quite often the case that the reaction with the fluid containing suspect antigen does not result in easily visualized agglutination products evidencing that reaction. It is thought that at least a partial reason for this is that adsorption onto the particle is too weak a bonding mechanism to enable complete utilization of the particles. That is, some of the adsorbed protein would tend to be desorbed from the particle and while still reactive of course with its immuno partner would then not have its carrier particles attached to it. To the extent that such material is loosened from its particles the agglutination pattern is rendered less discernible.

There are techniques for attaching proteins and especially antigens and antibodies to solid polymers. Covalent bonding is one such and is described in the literature in U.S. Pat. No. 3,857,931 issued Dec. 31, 1974. In that patent the preparation of latex polymer reagents having a variety of proteins covalently linked to the polymeric particles is described using a water soluble carbodiimide as a condensing agent between the particle and the protein resulting in the formation of an amide. The reaction described is a direct reaction between the polymer and the protein with the carbodiimide acting as a catalyst for the reaction.

Other patents in the field discloe a wide variety of reactions ranging from direct reaction of polymeric materials having reactive groups with the protein unmediated by any catalyst (see for example U.S. Pat. No. 3,891,580) to conversion of the support material to a reactive form such as the thio derivative followed by a reaction with the protein (see U.S. Pat. No. 3,904,478) to the widespread use of various carbodiimides to mediate the reaction as represented by U.S. Pat. No. 3,857,931.

DESCRIPTION OF THE INVENTION

In accordance with the present invention a new attachment technique is described in which the attachment of the immunological reagent to the immunologically inert carrier material is achieved through covalent bonding and the entire linking group between the reagent and the particle additionally contains a spacer group. The spacer group is thought to permit various degrees of freedom of the reagent moiety from the surface of the particle and thereby lends enhanced specificity.

In general, the process for achieving the covalent bond is a two-step technique, the first of which involves reacting latex particles having a reactive carboxyl group with a diamine in the presence of an appropriate carbodiimide as the condensing agent. The resulting product when can be designated as the modified latex is an amide terminating in primary or secondary amino groups. This product is then reacted with the appropriate immunological reagent such as an antigen or antibody modified if necessary to contain amino groups, in the presence of a bifunctional aldehyde to result in the condensation of the amino groups of the immunological reagent to the amino groups of the modified latex via an intermediate aldehyde bridging moiety.

Schematically, the process of the present invention can be depicted as follows:

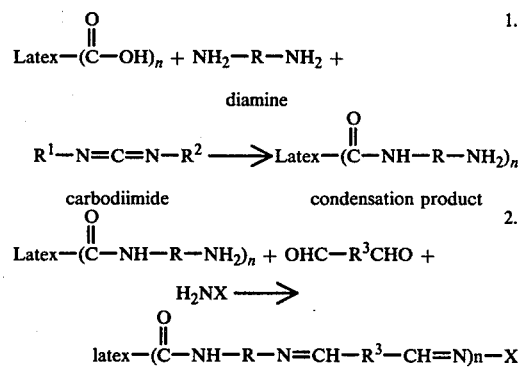

wherein n is an integer representing a plurality of carboxyl groups present in the polymeric latex, R is a straight or branched chain aliphatic hydrocarbon interrupted or non-interrupted and having 1–10 carbon atoms and especially alkylene, preferably hexamethylene but suitably also methylene, ethylene, propylene, isopropylene, butylene, sec. butylene and the like, or a dialkylene amine radical such as $-(CH_2)_x-NH-(CH_2)_y-$, in which x and y are integers from 1 to 3, most preferred among which is N,N dipropylene amine; $R_1$ and $R_2$ are cycloalkyl having from 5 to 6 carbon atoms in the ring; alkyl of from 2 to 12 carbon atoms, e.g., ethyl, n-propyl, isopropyl, n-butyl, sec.-butyl, isobutyl, tert.- butyl, amyl, hexyl, heptyl, octyl, nonyl, decyl, undecyl and dodecyl; monoarylsubstituted lower aklyl radicals, e.g., benzyl, α-and β-phenylethyl; monoaryl radicals, e.g., phenyl; morpholino; piperidyl; morpholinyl substituted lower aklyl radicals, e.g., ethyl morpholinyl; piperidyl substituted lower alkyl radicals, e.g., ethyl piperidyl; di-lower alkyamino; lower alkyl radicals; pyridyl substituted lower alkyl radicals, e.g., α, β and γ methyl or ethyl pyridyl; acid addition salts and quaternary amines thereof; and $R_3$ is alkylene of from 1–10 carbon atoms and preferably lower alkylene such as methylene, ethylene, n-propylene, n-butylene and the like. Preferred for $R^3$ is n-propylene, i.e., the dialdehyde glutaraldehyde, although suitable results are obtained with glyoxal and other members of the aliphatic dialdehyde class. Preferred carbodiimides are: 1-ethyl-3-(3'-dimethyl amino propyl) carbodiimide and 1-cyclohexyl-3-(2-morpholinoethyl) carbodiimide metho-p-toluenesulfonate. It should be understood, however, that any water soluble carbodiimide may be employed.

"Latex" signifies the residue of a water insoluble polymeric material containing carboxyl groups which is immunologically compatible with expected use conditions. The latex portion is preferably derived from ethylenically unsaturated polymers and especially from such polymers as:
polystyrene-butadiene,
polystyrene,
polystyrene with amino groups,
poly-acrylic acid,
poly-methacrylic acid,
acrylonitrile-butadiene, styrene copolymers,
polyvinyl acetate-acrylate,
polyvinyl pyridine,
vinyl-chloride acrylate copolymers, and the like.
Preferred for use in the invention are carboxylated styrenebutadiene polymer, polystyrene and acrylonitrile, butadienestyrene copolymers.

For use in the present invention, it is necessary that the latex either have carboxyl groups available for reaction or be capable of conversion to carboxyl derivatives. In addition, the latex material must be capable of being used in particulate form. With regard to physical characteristics of the polymers used per se it will be appreciated by those skilled in the art that particles which would have a tendency to agglomerate in an aqueous medium in the absence of immunological reaction should not be used. It has been found that particle sizes in the range of 0.05 to 1.0 and preferably 0.1 to 0.5 microns for those preferred materials listed above are suitable for use in practicing the invention. Other polymers having the appropriate electrostatic charge may be selected to avoid any spontaneous agglomeration. In addition, the quantity of carboxyl groups in the latex is an important characteristic in achieving sufficient condensation in the first diamine reaction step. It has been found suitable if the latex contains from 1 to 5 weight percent carboxyl groups and preferably 2 to 4 weight percent based on weight of the entire latex formulation on a dry basis. From this information, one could calculate the number of carboxyl groups per unit weight of polymer, and if the number of particles per unit weight were known, the number of carboxyl groups per particle could be calculated.

By "$H_2N-X$" in the foregoing reaction scheme is meant any immunological substance having at least one amino group present, X making up the rest of the molecule. The immunlogical substance may be a proteinaceous material such as a glycoprotein having terminal amino groups present, chemicals, drugs, hormones, haptens and the like. Therefore, the "X" portion of the immunological substance is not really relevant to the invention. It may constitute any residue of an immunological material, the critical factor being that the entire substance itself contains a reactive nitrogen atom supplied by an amino group. The materials of primary interest here are antigens or antibodies derived from proteins or hormones. Most preferred is human chorionic gonadotrophin (HCG) which contains significant numbers of amino groups. Other materials may be used such as those typified by hepatitis antigens, rubella antigen; immunoglobulins such as IgG, IgA and IgE, and a wide variety of serum proteins.

Dealing with each phase of the reaction scheme separately, it will be seen that Step 1 is basically a condensation reaction in which the diamine is reacted with the carboxyl group of the latex polymer. The reaction is suitably conducted at temperatures ranging from 4° C. to 37° C. preferably 15° C. to 25° C. with room temperature being most preferred. The reaction is carried out preferably in an aqueous medium with a concentration of solids which is conveniently handled. Suitably, the reaction mixture contains 1 to 35 and preferably 4 to 20 percent polymer solids. Since the bifunctionality of the diamine and the presence of many reactive sites both on the carboxylated latex itself and on the first reaction product between the diamine and the latex, could result in undesirable crosslinking, an excess of the diamine is used. The extent of this excess depends in a large measure on the particular latex and diamines selected and in addition is related to the concentration of carbodiimide used. The use of relatively large amounts of carbodiimide would tend to drive the reaction toward cross-linking in which case very large amounts of diamine would be necessary. Therefore, it is most preferred to minimize the amounts of carbodiimide so as to enable the use of moderate excess of diamine. For the most preferred diamines of the invention, at least 15 $NH_2$ groups per carboxyl group provides suitable results. Most preferred is 25–35 groups per carboxyl group. In this regard, it should be noted that the starting latex in the instant procedure is in the form of discrete particles. An undesirable extent of cross-linking would be evidenced by gel formation in the reaction product rather than discrete particle formation. The amount of carbodiimide used is itself interrelated with the amounts of diamines employed. It should be noted that the effect of the carbodiimide is to activate the carboxyl groups. Thus, it is desirable to ensure activation of as many of these groups as possible to enable maximum subsequent attachment of protein to the particle. Therefore, an excess of carbodiimide is employed relative to the carboxyl groups present. For the preferred materials, the preferred amounts are at least 10 carbodiimide molecules per carboxyl group and preferably 15–35 molecules per group. Ordinarily, the reaction is completed in several hours and results in a solid product in discrete particle form modified in accordance with the reaction scheme presented above. Side reactions and further reaction between the modified latex and unreacted latex is minimized when the preferred parameters of this invention are employed.

In addition, the above reaction is preferably carried out under neutral or mildly alkaline conditions using a pH in the range of 7.5 to 9 with 8 to 8.6 being preferred. Suitable buffer systems may be employed with sodium borate — boric acid, or sodium phosphate being preferred among the many buffers normally used in physiological systems.

After preparation, the final product is suitably washed and dried if desired, care being taken to avoid drastic conditions that could alter proteinaceous materials. The final product is then available for conversion in accordance with Reaction No. 2 which is the key to the covalent attachment of the immunological substance to the modified latex. The numerous amino groups attached to the latex surface are the means by which covalent bonding to the available amino group of the immunological reagent is achieved via the dialdehyde.

The reaction described in Step 2 is conducted preferably in an aqueous medium at a pH range from 7.0 to 9.0 and preferably 7.5 to 8.0 at a solid concentration preferably of approximately 2 to 10 percent. The amount of aldehyde used is suitably based on the stoichiometry of the reaction, one mole of the aldehyde being needed for every amino group present in the modified latex. Suitably, an excess of the aldehyde is employed such that the reaction between the amino groups on the immunological reagent and the amino groups on the latex is sufficiently complete. The difficulty in monitoring the process at this point is that from an economic standpoint as much of the immunological material should get onto the latex as is possible without any appreciable cross-linking taking place. In general, if the preferred aspects of the invention are followed, this will be minimized. In addition, it is preferred that the aldehyde be added to a mixture of the immunological material and the modified latex to avoid cross-linking either of the reactants between themselves.

The temperature of the reaction is generally in the range of room temperature to 80° C. with 50° C. to 60° C. being preferred. An incubation period after cooling down to room temperature is then preferably used. Periods of 10 hours or more are suitable. Care should be exercised in any reactions, or incubations involving proteins because of the denaturing phenomenon. The resulting product from the reaction is a solid particulate latex to which is covalently bonded an immunological reagent through a diamine and dialdelyde bridging group. The dialdehyde provides the bridge attachment between the immunological reagent and the latex particle and thus forms the spacer group to which reference was made above. The product can then be used in a wide variety of diagnostic tests depending of course on the particular immunological reactant attached. In use, the reagent suitably is employed in an aqueous medium and comprises from 0.5 to 5.0 and preferably 1.0 to 3.0 by weight based on the weight of the entire composition. The actual concentration used will vary depending upon the nature of the diagnostic test used, the types of particles employed and a variety of other factors.

As an alternative to Reaction 1 and 2 described above and this is particularly so in dealing with immunological substances having an abundance of carboxyl groups themselves, it is oftentimes appropriate to convert the carboxyl groups of the immunological substance to the diamine in accordance with the reaction as designated in 1 above. Thus, for example, HCG which is an acidic glycoprotein with numerous carboxyl groups can be converted to a more reactive amine and the resulting condensation product reacted with a modified latex via the dialdehyde bridging moiety.

The invention will now be described in terms of specific embodiments thereof as set forth in the following examples:

EXAMPLE 1.

Preparation of a latex particle to which the hormone HCG is attached.

Carboxylated polystyrene-butadiene particles having 20% butadiene obtained from the Rhone Progil Corporation as PSI 83 (3 weight percent COOH, 0.2 micron diameter, 10% solids) are diluted in 0.05M borate buffer, pH 8.7, to a concentration of 8%. Two volumes of the 8% latex are then mixed with one volume of 1.0M 1-ethyl-3-(3'-dimethyl amino propyl) carbodiimide·HCl and one volume of 1.0M (3-3'diamino) dipropyl amine and mixed at ambient temperature for one hour. The reaction mixture is then dialyzed exhaustively with 0.05M imidazole buffer, pH 7.6, containing 2% sodium chloride. The latex concentration following dialysis is adjusted to 4% with imidazole buffer. Three volumes of the 4% diamino latex derivative are then mixed with two volumes of human chorionic gonadotropin (0.75 mg/ml) and one volume of 0.25% glutaraldehyde. Both the human chorionic gonadotropin and the 0.25% glutaraldehyde are made in 0.05M imidazole buffer — pH 7.6 containing 2% NaCl. This mixture is then incubated at 56° C. for 1.5 hours after which it is incubated for 18 hours at room temperature. It is then washed clear of soluble reactants and soluble reactive byproducts by high speed centrifugation (30-35,000 x g for 20 minutes). The resultant washed latex containing human chorionic gonadotropin is resuspended to a final particle concentration of 1-2% for use as a latex antigen in an immunochemical pregnancy test.

EXAMPLE 2

Preparation of latex particle suspensions to which a diamino derivative of HCG is attached.

The diamino derivative of HCG is prepared by reacting two volumes of HCG (1.5 mg/ml) dissolved in a 0.05M Borate buffer, pH 8.7, with one volume of 1M carbodiimide, and one volume of 1M (3,3'diamino) dipropyl amine (both dissolved in 0.05M Borate buffer, pH 8.7). The reaction is carried out at 18 to 25° C. for 1.5 hours after which time the mixture is thoroughly dialyzed against distilled water to remove unreacted diamine. This HCG diamino derivative is recovered and can be stored at −20° C. for up to 24 hours to be used for reaction with processed latex suspensions.

The reaction of the HCG diamino derivative with processed latex suspensions nd glutaraldehyde, takes place as shown in Example 1 above.

EXAMPLE 3.

Preparation of a latex particle to which the hormone human chorionic gonadotropin is attached.

Carboxylated Styrene-Butadiene particles obtained from Rhone Poulenc Polymers as PSI 83 (3% COOH, 0.2 micron dimater, 10% solids) are diluted in 0.05M borate buffer, pH 8.7, to a concentration of 8%. Two volumes of 8% latex are then mixed with one volume of 0.7M 1-Ethyl-3-(3'-dimethyl amino propyl) carbodiimide·HCl (CDI) and one volume of 1.3M ethylene diamine and mixed at ambient temperature for one hour. The reaction mixture is then dialyzed exhaustively with 0.05M Imidazole buffer-pH 7.6 containing 2% sodium chloride, and thereafter the latex concentration is adjusted to 4% with the same buffer. Three volumes of the 4% diamino latex derivative are then mixed with two volumes of human chorionic gonadotropin (0.75 mg/ml) and one volume of 0.25% glutaraldehyde. Both the human chorionic gonadotropin and the 0.25% glutaraldehyde are made in 0.05M Imidazole buffer-pH 7.6 containing 2% NaCl. This mixture is then incubated at 56° C. for one hour after which it is washed clear of soluble reactants and soluble reactive byproducts by high speed centrifugation (30–35,000 × g for 20 minutes). The resultant washed latex containing human chorionic gonadotrophin is resuspended to a final particle concentration of 1–2% for use as a latex antigen in an immunochemical pregnancy test. When the above procedure is repeated using CDI in the range of 1.3M to 0.7M and the ethylene diamine at 0.7M to 1.3M suitable results are obtained.

EXAMPLE 4.

Preparation of a latex particle to which the hormone human chorionic gonadotropin is attached.

Carboxylated Styrene-Butadiene particles obtained from Dow Chemicals, 0.25 micron diameter; 2% COOH (0.25 meq. COOH/g dry particles); product code 47609 are diluted in 0.05M borate buffer, pH 8.7, to a concentration of 8%. Two volumes of 8% latex are then mixed with one volume of 10mM 1-Ethyl-3-(3'-dimethyl amino propyl) carbodiimide HCl (CDI) and one volume of 10mM (3-3'-diamino) dipropyl amine and mixed at ambient temperature for one hour. The reaction mixture is then dialyzed exhaustively with 0.05M Imidazole buffer-pH 7.6 containing 2% sodium chloride, and thereafter the latex concentration is adjusted to 4% with the same buffer. Three volume of the 4% diamino latex derivative are then mixed with two volumes of human chorionic gonadotropin (0.75 mg/ml) and one volume of 0.25% glutaraldehyde. Both the human chorionic gonadotropin and the 0.25% glutaraldehyde are made in 0.05M Imidazole buffer-pH 7.6 containing 2% NaCl. This mixture is then incubated at 56° C. for one hour after which it is washed clear of soluble reactants and soluble reactive byproducts by high speed centrifugation (30–35,000 733 g for 20 minutes). The resultant washed latex containing human chorionic gonadotropin is resuspended to a final particle concentration of 1–2% for use as a latex antigen in an immunochemical pregnancy test. When the range of CDI and diamine are each varied from 10 to 25 mM, suitable results are obtained.

EXAMPLE 5

Preparation of a latex particle to which the hormone human chorionic gonadotropin is attached.

Carboxylated Styrene-Butadiene particles obtained from Rhone Poulenc Polymers as PSI 83 (3% COOH, 0.2 micron diameter, 10% solids) are diluted in 0.05M borate buffer, pH 8.7, to a concentration of 8%. Two volumes of 8% latex are then mixed with one volume of 1.0M 1-Ethyl-3-(3'-dimethyl amino propyl) carbodiimide HCl and one volume of 1.0M (3-3'diamino) dipropyl amine and mixed at ambient temperature for one hour. The reaction mixture is then dialyzed exhaustively with 0.05M Imidazole buffer-pH 7.6 containing 2% sodium chloride, and thereafter the latex concentration is adjusted to 4% with the same buffer. Three volumes of the 4% diamino latex derivative are then mixed with two volumes of human chorionic gonadotropin (0.75 mg/ml) and one volume of 0.25% glutaraldehyde. Both the human chorionic gonadotropin and the 0.25% glyoxaldehyde are made in 0.05M Imidazole buffer-pH 7.6 containing 2% NaCl. This mixture is then incubated at 56° C. for one hour after which it is washed clear of soluble reactants and soluble reactive byproducts by high speed cnetrifugation (30–35,000 × g for 20 minutes). The resultant washed latex containing human chorionic gonadotropin is resuspended to a final particle concentration of 1–2% for use as a latex antigen in an immunochemical pregnancy test.

EXAMPLE 6

Preparation of a latex particle to which the hormone human chorionic gonadotropin is attached.

Carboxylated Styrene-Butadine particles obtained from Rhone Poulene Polymers as PSI 83 (3% COOH, 0.2 micron diameter, 10% solids) are diluted in 0.05M borate buffer, pH 8.7, to a concentration of 8%. Two volumes of 8% latex are then mixed with one volume of 0.7M 1-Ethyl-3-(3'-dimethyl amino propyl) carbodiimide HCl and one volume of 1.3m (1,6) hexanediamine and mixed at ambient temperature for one hour. The reaction mixture is then dialyzed exhaustively with 0.05M Imidazole buffer-pH 7.6 containing 2% sodium chloride, and thereafter the latex concentration is adjusted to 4% with the same buffer. Three volumes of the 4% diamino latex derivative are then mixed with two volumes of human chorionic gonadotropin (0.75mg/ml) and one volume of 0.25% glutaraldehyde. Both the human chorionic gonadotropin and the 0.25% glutaraldehyde are made in 0.05M Imidazole buffer-pH 7.6 containing 2% NaCl. This mixture is then incubated at 56° C. for one hour after which it is washed clear of soluble reactants and soluble reactive byproducts by high speed centrifugation (30–35,000 × g for 20 minutes). The resultant washed latex containing human chorionic gonadotropin is resuspended to a final particle concentration of 1–2% for use as a latex antigen in an immunochemical pregnancy test.

EXAMPLE 7

In each of the foregoing examples, the polymeric latex material can be replaced by styrene-butadiene particles having a particle size of 0.21 and 0.25 microns and 2% and 3% carboxyl group content.

What is claimed is:

1. An immunological test reagent having the formula:

$$\text{latex}-(C(=O)-NH-R-N=CH-R^3-CH=N)_n-X$$

wherein latex is the residue of a water insoluble ethylenically unsaturated polymeric material containing carboxyl groups and n is an integer corresponding to a plurality of those carboxyl groups present in the polymeric latex, R is a straight or branched chain alkylene or a dialkylene amine radical having 1–10 carbon atoms, $R^3$ is alkylene having from 1–10 carbon atoms and X is the residue of an immunological substance containing at least one amino group.

2. The reagent of claim 1 in discrete particle form.

3. The reagent of claim 1 wherein R is the N, N dipropylene amine radical.

4. The reagent of claim 3 wherein the ethylenically unsaturated polymer is carboxylated styrenebutadiene polymer.

5. The reagent of claim 4 wherein $R^3$ is the propylene radical.

6. The reagent of claim 5 wherein the immunological substance is human chorionic gonadotropin.

7. The reagent of claim 6 in an aqueous medium wherein said latex reagent is present at from 0.5 to 5.0 percent by weight of the entire composition.

8. The process for producing a compound of the formula:

$$\text{latex-}(\overset{O}{\overset{\|}{C}}-NH-R-N=CH-R^3-CH=N)_{n-x}$$

wherein latex is the residue of a water insoluble ethylenically unsaturated polymeric material containing carboxyl groups and n is an integer corresponding to a plurality of those carboxyl groups present in the polymeric latex, R is a straight or branched chain alkylene or a dialkylene amine radical having 1-10 carbon atoms, $R^3$ is alkylene having from 1-10 carbon atoms and X is the residue of an immunological substance containing at least one amino group which comprises contacting a carboxylated latex of the formula $$\text{latex-}(\overset{O}{\overset{\|}{C}}-OH)_n$$

with a diamine of the formula $$NH_2-R-NH_2$$

in the presence of a water soluble carbodiimide condensing agent to produce a condensation product having the formula $$\text{latex-}(\overset{O}{\overset{\|}{C}}-NH-R-NH_2)_n$$

and thereafter contacting said condensation product with a dialdehyde of the formula $$OHC-R^3CHO$$

in the presence of a compound of the formula $$H_2NX$$

wherein X is the residue of immunological substances containing at least one amino group.

9. The process of claim 8 wherein said carbodiimide has the formula $$R_1-N=C=N-R_2$$

wherein $R_1$ and $R_2$ are cycloalkyl having from 5 to 6 carbon atoms in the ring, alkyl of from 2 to 12 carbon atoms, monoarylsubstituted lower alkyl radicals, monoaryl radicals, morpholinyl substituted lower alkyl radicals, lower alkyl radicals, pyridyl substituted lower alkyl radicals, acid addition salts and quaternary amines thereof.

10. The process of claim 9 wherein said carbodiimide compound is 1-ethyl-3-(3'-dimethyl amino propyl) carbodiimide or 1-cyclohexyl-3-(2-morpholinoethyl) carbodiimide metho-p-toluenesulfonate.

11. The process of claim 8 wherein said diamine is 3-3' diamino dipropyl amine or hexamethylene diamine.

12. The process of claim 8 wherein the latex is in discrete particle form and is derived from an ethylenically unsaturated polymer containing carboxyl groups.

13. The process of claim 12 wherein the polymer is carboxylated poly-styrene-butadiene.

14. The process of claim 8 wherein the dialdehyde is glutaraldehyde.

15. The process of claim 8 wherein the $H_2NX$ is human chorionic gonadotropin or human chorionic gonadotropin previously reacted to convert its carboxylic acid groups to amino groups.

16. The process of claim 10 wherein the diamine is 3,3' diamino dipropyl amine or hexamethylene diamine, the latex is in discrete particle form and is derived from an ethylenically unsaturated polymer, the dialdehyde is glutaraldehyde and $NH_2X$ is human chorionic gonadotropin or human chorionic gonadotropin previously reacted to convert its carboxylic acid groups to amino groups.

17. The process of claim 16 wherein the quantity of carboxyl groups present in the carboxylated latex is from 1-5 percent by weight based on the dry weight of the latest formulation, the carbodiimide is used at a level in excess of 10 molecules per carboxyl group, the diamine is used at a level sufficient to supply at least 15 amino groups per carboxyl group, and the dialdehyde is used at a level in excess of one mole per amino group present in the condensation product.

18. The process of claim 17 wherein the latex particle size is in the range of 0.05 to 1 microns.

* * * * *

UNITED STATES PATENT AND TRADEMARK OFFICE
CERTIFICATE OF CORRECTION

PATENT NO. : 4,140,662
DATED : 2/20/79
INVENTOR(S) : Rudolph P. Reckel, et al.

It is certified that error appears in the above-identified patent and that said Letters Patent are hereby corrected as shown below:

At Column 2, line 13, "field discloe" should be -- field disclose --.
At Column 2, line 40, "product when" should be -- product which --.
At Column 6, line 60, "suspensions nd" should be -- suspensions and --.
At Column 7, line 51, "(30-35,000 733" should be -- (30-35,000 --.

Signed and Sealed this

Eleventh Day of March 1980

[SEAL]

Attest:

SIDNEY A. DIAMOND

Attesting Officer

Commissioner of Patents and Trademarks